(12) United States Patent
Janssen et al.

(10) Patent No.: US 10,716,431 B2
(45) Date of Patent: Jul. 21, 2020

(54) BEVERAGE AND FOOD TEMPERATURE REGULATION

(71) Applicant: KONINKLIJKE PHILIPS N.V., Eindhoven (NL)

(72) Inventors: Jozef Johannes Maria Janssen, Eindhoven (NL); Arjan Teodor Van Wieringen, Eindhoven (NL); Christian Marie Frans Jozef Senden, Eindhoven (NL); Arnold Aalders, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 189 days.

(21) Appl. No.: 15/525,331

(22) PCT Filed: Oct. 28, 2015

(86) PCT No.: PCT/EP2015/074915
§ 371 (c)(1),
(2) Date: May 9, 2017

(87) PCT Pub. No.: WO2016/074920
PCT Pub. Date: May 19, 2016

(65) Prior Publication Data
US 2017/0332836 A1    Nov. 23, 2017

(30) Foreign Application Priority Data
Nov. 11, 2014 (EP) .................................... 14192712

(51) Int. Cl.
*A47J 36/24* (2006.01)
*G05D 23/19* (2006.01)
*A61B 5/00* (2006.01)

(52) U.S. Cl.
CPC ...... *A47J 36/2411* (2013.01); *G05D 23/1919* (2013.01); *A61B 5/4809* (2013.01)

(58) Field of Classification Search
CPC . A47J 36/2411; A47J 36/2433; A61B 5/4809; G05D 23/1919
See application file for complete search history.

(56) References Cited

U.S. PATENT DOCUMENTS

| 6,617,552 B1 * | 9/2003 | Taylor ................. A47J 36/2433 219/386 |
| 2004/0140304 A1 * | 7/2004 | Leyendecker ...... A47J 36/2433 219/386 |

(Continued)

FOREIGN PATENT DOCUMENTS

| DE | 202011088015 A1 | 6/2013 |
| EP | 1025786 A1 | 8/2000 |

(Continued)

*Primary Examiner* — Nelson J Nieves

(57) ABSTRACT

A device for food and/or beverage temperature regulation includes a cooler for providing a cooling mode in which the food and/or beverage is cooled, a heater for providing a heating mode in which the food and/or beverage is heated, and a pre-heating mode in which the food and/or beverage is pre-heated. A controller is configured to control the cooler and heater. The controller is further configured to activate the cooling or heating mode in response to signals indicative of a change in the behavior of a recipient of the food and/or beverage, and to activate the pre-heating mode in response to predicted behavior. The signals may represent sound and/or movement and may originate from sensors, such as microphones and/or radar sensors.

20 Claims, 3 Drawing Sheets

(56) References Cited

U.S. PATENT DOCUMENTS

| | | | |
|---|---|---|---|
| 2005/0045617 A1* | 3/2005 | Taylor | A47J 36/2433 |
| | | | 219/400 |
| 2007/0156060 A1 | 7/2007 | Cervantes | |
| 2007/0223895 A1* | 9/2007 | Flemm | A47J 36/2433 |
| | | | 392/441 |
| 2009/0208193 A1 | 8/2009 | Bauer | |
| 2010/0058776 A1 | 3/2010 | Loibl | |
| 2014/0058256 A1 | 2/2014 | De Jong | |
| 2014/0085093 A1 | 3/2014 | Mittleman | |
| 2015/0068720 A1* | 3/2015 | Lipoma | A47J 36/2411 |
| | | | 165/222 |

FOREIGN PATENT DOCUMENTS

| | | |
|---|---|---|
| JP | 2005110938 A | 4/2005 |
| JP | 2006303898 A | 11/2006 |
| JP | 2006303989 A | 11/2006 |
| WO | 20088048571 A2 | 4/2008 |
| WO | 2013093686 A1 | 6/2013 |

* cited by examiner

BEVERAGE AND FOOD TEMPERATURE REGULATION

This application is the U.S. National Phase application under 35 U.S.C. § 371 of International Application No. PCT/EP2015/074915, filed on Oct. 28, 2015, which claims the benefit of International Application No. 14192712.9 filed on Nov. 11, 2014. These applications are hereby incorporated by reference herein.

FIELD OF THE INVENTION

The present invention relates to beverage and food temperature regulation. More in particular, the present invention relates to a device and method for regulating the temperature of beverages, such as milk, or food, such as vegetables, so as to keep a beverage or food at a relatively low storage temperature and to later warm the beverage or food.

BACKGROUND OF THE INVENTION

It is well known to keep a milk bottle for a baby in a refrigerator and to heat the milk bottle in a microwave oven when the baby wakes up. This known method requires two devices and also requires both the baby and the parent to wait until the milk has reached the proper temperature. As babies generally are not appreciative of waiting and are perfectly capable of making this known, this method is far from ideal.

United States Patent Application US 2004/0140304 discloses a device for both chilling and warming a baby bottle. This known device utilizes a thermoelectric module, also known as Peltier element, both for chilling and warming. A clock circuit can be set to an activation or target time to automatically switch the device from a chilling mode to a warming mode at the activation time. A buzzer may sound when the target time has arrived. The known device can also manually be switched into the warming mode.

This known device has the disadvantage that the activation time must be known in advance. If the known device has the bottle ready before the baby is awake, and the parent is woken up by the device's buzzer, then the baby has to be woken up and will not be amused. If, however, the baby has already woken up and made her hunger known before the target time, then the parent has to manually switch the device into the warming mode and wait for the bottle to be ready while the baby is crying, leaving both the parent and the baby not amused.

International Patent Application WO 2013/093686 discloses an apparatus for monitoring a sleeping person and arranged for estimating the moment of waking up of the sleeping person. In an embodiment, a bottle heater may be started before a baby is about to wake up. The chilling of a bottle is however not disclosed in WO 2013/093686. In other words, the known apparatus is incapable of chilling the bottle before it is to be heated. In addition, the known apparatus is incapable of reversing the heating process in case a "false alarm" is produced and the baby fails to wake up, in which case the bottle may need to be chilled again.

SUMMARY OF THE INVENTION

It is an object of the present invention to solve these and other problems by providing a device and method for beverage and/or food temperature regulation which take user requirements into account, in particular the moment at which the recipient would like to receive their food or beverage, and which is not limited to heating alone.

Accordingly, the present invention provides a device for food and/or beverage temperature regulation, comprising a cooling unit for providing a cooling mode in which the food and/or beverage is cooled, a heating unit for providing a heating mode in which the food and/or beverage is heated and for providing a pre-heating mode in which the food and/or beverage is pre-heated, a memory unit for storing behavioral pattern data of the recipient, a prediction unit for predicting, using the behavioral pattern data, the future behavior of the recipient, and a control unit for controlling the cooling unit and the heating unit, wherein the control unit is arranged for:
   receiving at least one signal indicative of the current behavior of the recipient of the food and/or beverage,
   detecting a change in said current behavior, and
   activating the cooling mode or the heating mode in response to said detecting, and
   activating the pre-heating mode in response to the future behavior predicted by the prediction unit.

By switching between the modes in dependence on detecting a change in the behavior of the intended recipient of the food and/or beverage, the point in time at which the item is ready will be much better aligned with the desire of the recipient, that is, the consumer. As a result, the recipient will be more satisfied and the device will be used more efficiently as heating the food and/or beverage long before the moment of consumption may be avoided, for example. Avoiding prolonged heating not only saves energy, it also improves the quality of the food and/or beverage.

By activating the pre-heating mode in response to the future behavior predicted by the prediction unit, the point in time at which the item is ready will be even better aligned with the desire of the recipient since the heating mode will require less time as a result.

Detecting a change in the current behavior of the recipient can be carried out on the basis of at least one signal indicative of the behavior of the recipient of the food and/or beverage. These signals may be produced by sensor units, for example a microphone unit for providing acoustic signals (such as signals representing sound produced by the recipient), a radar unit and/or a camera unit for producing signals representing movement and/or the posture of the recipient, and a radar unit and/or a pressure sensor unit for producing signals representing vital signs of the recipient, such as the recipient's heartbeat and/or respiration rate. In the case of babies, for example, a moisture detection unit for producing signals representing moisture loss of the recipient may be advantageous. The sensor units are preferably located near the recipient, for example within a few meters, or placed on the recipient's body. Some sensors, such as pressure sensors for sensing movement and/or posture, or moisture sensors, may be placed in or on the recipient's bed or seat, possibly in addition to placement on or near the recipient's body.

By detecting a change in the behavior of the recipient of the food or beverage, it is possible to predict the recipient's behavior to a certain extent. For example, an increase in the recipient's movements is likely to indicate that the recipient is about to get up when lying down or seated, or wake up when asleep. In this way, it is possible to anticipate the desire for the consumption and even predict when the recipient will want their consumption.

The accuracy of the prediction can be improved by using historical data related to the recipient. To this end, the device of the present invention further comprises a memory unit for storing behavioral pattern data of the recipient and a prediction unit for predicting, using the behavioral pattern data, the future behavior of the recipient. The behavioral pattern data may be derived from received behavior signals and may then be stored. The behavioral pattern data may also be obtained from another device and then be stored in the device of the present invention.

Although the prediction unit may be used to predict a change in behavior and hence a desire to consume food and/or beverage without sensor input, it is preferred that the control unit is arranged for weighing signals using the behavior predicted by the prediction unit. That is, the behavior predicted on the basis of historical data, such as sleeping patterns, may be used to weigh signals representing e.g. movement. As a result, increased body movement will receive more weight, and will thus form a greater indication of the recipient's waking up, when this matches the historically predicted behavior at that point in time.

Although the invention has been explained above with reference to two modes, a heating mode and a cooling mode, the invention is not so limited and in an advantageous embodiment the heating unit is further arranged to provide a pre-heating mode, and wherein the control unit is arranged for activating the pre-heating mode in response to the behavior predicted by the prediction unit. Embodiments can also be envisaged which additionally, or alternatively, offer a pre-cooling mode. Some embodiments may provide an inactive mode in which the device neither heats (or pre-heats) nor cools (or pre-cools). In such embodiments, the device may switch between three (or five) modes: heating, inactive and cooling (or pre-heating, heating, inactive, pre-cooling and cooling). Accordingly, in embodiments of the invention the control unit may be arranged for de-activating the cooling mode or the heating mode in response to the future behavior predicted by the prediction unit. It will be understood that activating one mode, for example the pre-heating mode, implies deactivating another mode, for example the cooling mode or inactive mode. It will further be understood that activating or de-activating a mode in response to the predicted future behavior implies that the activation or de-activation is only carried out if triggered by the predicted future behavior and may not be carried out if the predicted future behavior does not trigger an activation or de-activation. A trigger event in the predicted future behavior may, for example, be a habit of waking up at a certain time.

The present invention also provides a method for food and/or beverage temperature regulation using a cooling unit for providing a cooling mode in which the food and/or beverage is cooled and a heating unit for providing a heating mode in which the food and/or beverage is heated and for providing a pre-heating mode in which the food and/or beverage is pre-heated, the method comprising the steps of:
  storing behavioral pattern data of the recipient,
  predicting, using the behavioral pattern data, the future behavior of the recipient,
  receiving at least one signal indicative of the current behavior of the recipient of the food and/or beverage,
  detecting a change in said current behavior,
  activating the cooling mode or the heating mode in response to said detecting, and
  activating the pre-heating mode in response to the predicted future behavior.

The present invention additionally provides a software program product for causing a processor to carry out the method steps mentioned above. The software program product may be stored on a tangible carrier, such as a DVD or a USB stick. Alternatively, the software program product may be stored on a server from which it may be downloaded using the Internet. The software program product contains software instructions which can be carried out by the processor of a device, such as a server, a user device (for example a smartphone), and/or a monitoring device.

BRIEF DESCRIPTION OF THE DRAWINGS

The present invention will further be explained with reference to exemplary embodiments illustrated in the drawings, in which.

DETAILED DESCRIPTION OF THE EMBODIMENTS

Figure 1:
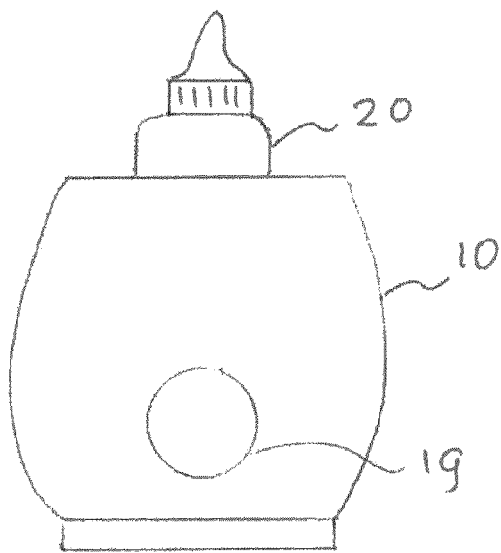
FIG. 1 schematically shows a merely exemplary embodiment of a device according to the present invention.

The merely exemplary device 10 according to the present invention shown in FIG. 1 is designed for cooling and warming bottles, such as milk bottles. To this end, the device 10 has a hollow interior into which a bottle, such as a milk bottle 20, can be inserted. The device 10 of FIG. 1 is shown to have a manual control knob 19 which may allow manually overriding any automatic controls and which may further allow setting desired temperatures. While the embodiment of FIG. 1 is designed for holding milk bottles for infants, other embodiments may be adapted to cool and warm other containers, such as food containers or larger bottles. Some embodiments may not have a hollow interior but may for example have a top surface that may be cooled and heated.

Figure 2:
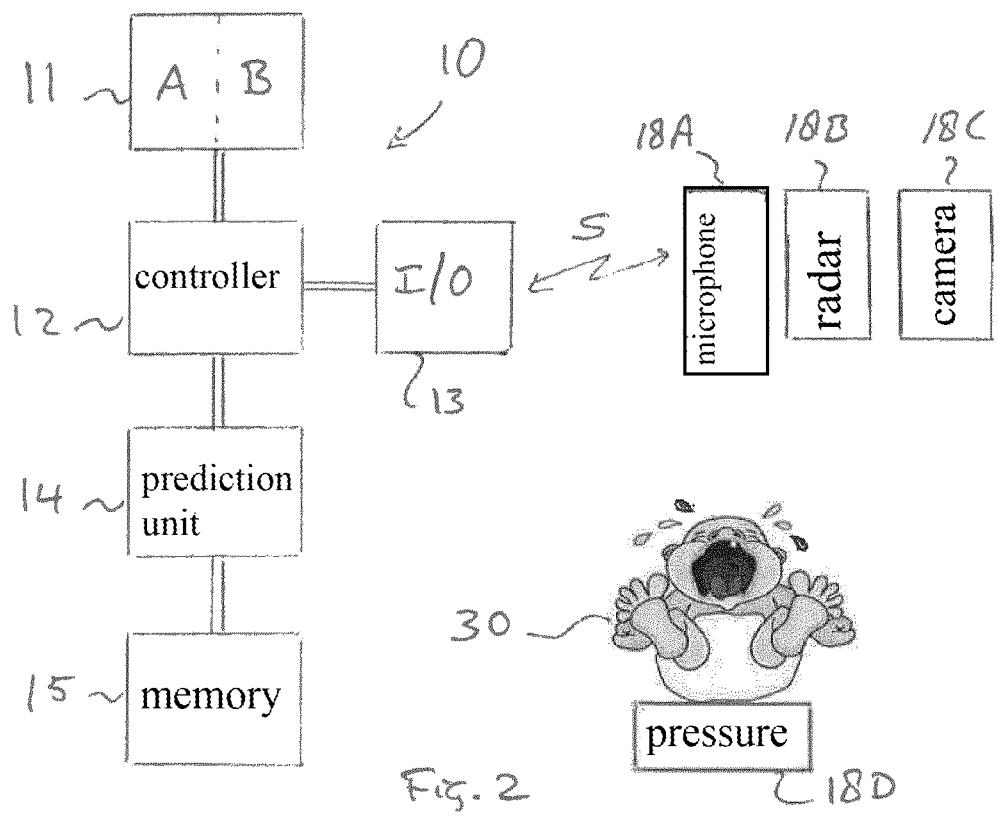
FIG. 2 schematically shows a merely exemplary embodiment of a device according to the present invention in more detail.

The functional components of an exemplary embodiment of a device 10 are shown in FIG. 2. The device illustrated in FIG. 2 comprises a combined cooling and heating unit 11, a control unit 12, an input/output unit 13, a prediction unit 14 and an associated memory unit 15. The cooling and heating unit 11 comprises a cooling unit 11A providing a cooling mode in which the food and/or beverage is cooled and a heating unit 11B for providing a heating mode in which the food and/or beverage is heated. In the embodiment shown, the cooling and heating unit 11 is constituted by a single combined unit which comprises a Peltier element. As is well known, Peltier elements (or thermoelectric elements) are capable of generating or removing heat, depending on the polarity of the applied voltage. Instead of a combined unit, however, separate heating and cooling units may also be used.

The control unit 12, which will later be explained in more detail with reference to FIG. 3, controls the heating and/or cooling of the heating and cooling unit 11, in response to signals received from sensor units 18A-18D. The control unit 12 is connected with an input/output (I/O) unit 13, which may comprise an antenna for wirelessly receiving signals from the sensor units.

In the embodiment shown, the device 10 also comprises a prediction unit 14 and an associated memory unit 15. The prediction unit 14 may be a processor that serves to predict the behavior of the recipient 30 based on previous behavior stored in the memory 15. That is, the memory 15 stores historical data with respect to the behavior of the recipient 30, for example the points in time at which the recipient 30 woke up during the past days, weeks or months. Additionally, or alternatively, the memory 15 may store for a plurality of moments per day (or other time unit) the particular behavior of the recipient as determined from the signals received from the sensor units 18.

The prediction unit or processor 14 is arranged for predicting, at a particular point in time, the behavior of the recipient 30, based upon the past behavior stored in the memory 15 and/or present behavior. The control unit 12 may then use this predicted behavior to weigh the information received from the sensor units. For example, if the information received from the sensor units (e.g. "increasing movement") matches the typical behavior at the particular point in time (e.g. "will normally wake up in about 5 minutes") then the controller can for example start warming a previously cooled bottle.

The sensor units 18 shown merely by way of non-limiting example in FIG. 2 comprise a microphone unit 18A for receiving sound produced by the recipient (or consumer) 30 of the food and/or beverage, a radar unit 18B for receiving movement and/or life sign information of the recipient 30, a camera 18C for receiving image information relating to movement and/or posture, and a pressure sensor 18D for receiving pressure information which may be indicative of movement and/or posture. Not all of these sensor units need be present, while in other embodiments further sensor units may be present, such as a moisture sensor unit. All sensor units are arranged for transmitting signals to the I/O unit 13 of the control unit 13, either wirelessly (using e.g. Bluetooth® or Wi-Fi) or via a suitable wired connection.

With regard to the radar unit 18B it is noted that for example United States Patent Application US 2014/0058256 discloses a radar apparatus for detecting vital signs of a subject. In particular, the radar apparatus is arranged for performing a radar measurement of a superficial artery structure so as to retrieve heart activity information. Such a radar apparatus may advantageously be used as a sensor unit in the present invention.

Figure 3:
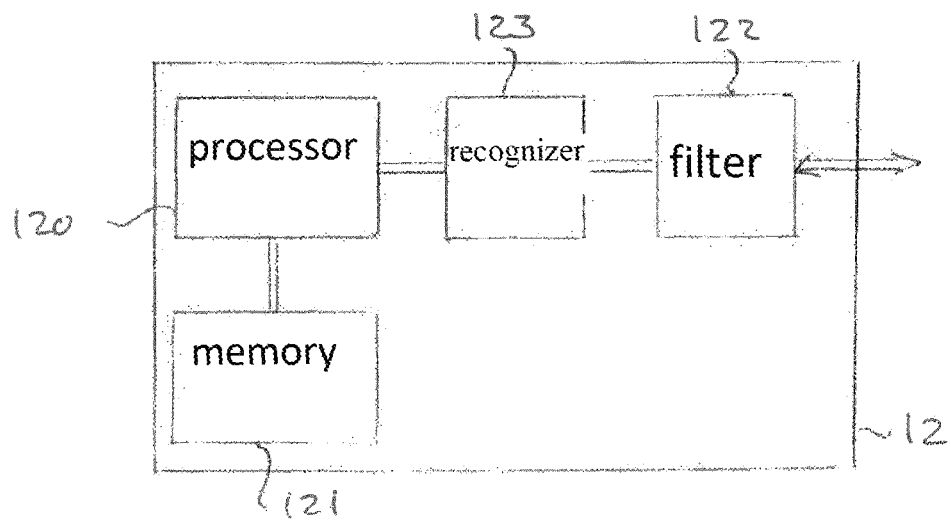
FIG. 3 schematically shows an exemplary embodiment of a control unit of the device of FIG. 2 in more detail.

An exemplary embodiment of the control unit 12 is schematically illustrated in FIG. 3. The embodiment of FIG. 3 comprises a microprocessor 120 and an associated memory 121. It is noted that the processor memory 121 may be a separate memory from the prediction memory 15, but that in some embodiments both functions may share a common memory unit. The control unit 12 of FIG. 3 further comprises an (optional) audio filter unit 122 and/or an (optional) sound recognition unit 123. The audio filter unit 122 serves to filter the signal received from the microphone unit 18A so as to extract audio frequencies of interest. The sound recognition unit 123 serves to recognize sound, such as the sound of a baby crying. Both the audio filter unit 122 and the sound recognition unit 123 may be implemented in hardware, software or a combination of hardware and software.

The control unit 12 may comprise other components, such as an image recognition unit (not shown). Such units may also be implemented in hardware, software, or a combination. Suitable software programs may be stored in the memory 121 and be carried out by the processor 120.

The control unit 12 is arranged for detecting a change in the behavior of the intended recipient of the food and/or beverage on the basis of the received sensor signals and, optionally, also on the basis of stored behavioral data derived from previously received sensor signals. Detecting a change in one particular signal, such as a sound signal, may be sufficient for detecting a change in the behavior of the recipient, but preferably two or more signals are used as a basis for detecting behavioral change. Furthermore, the control unit 12 is arranged for switching between the cooling mode and the heating mode in response to said detecting a change in the behavior of the recipient.

Figure 4:
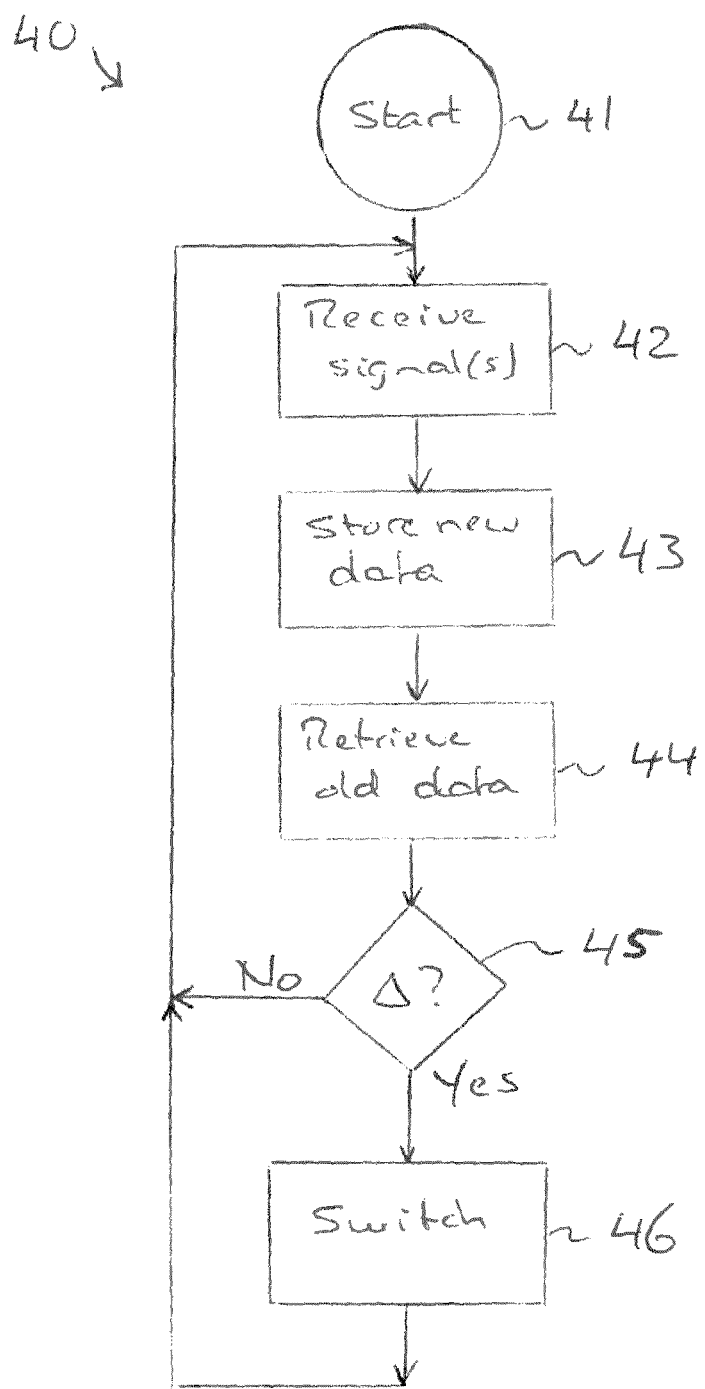
FIG. 4 schematically shows a flow diagram of an embodiment of a method according to the present invention.

An example of a method according to the present invention as may be carried out by the processor 120 is schematically illustrated in FIG. 4. The merely exemplary method 40 starts at step 41. In step 42, a behavior signal is received from one or more sensor units (18 in FIG. 2). In step 43, the relevant behavioral information may be stored as behavioral pattern data (in memory 15 illustrated in FIG. 2, for example). In step 44, this new behavioral information is compared with older behavioral information (which may be stored in memory 15 and may be retrieved in this step). In step 45, it is decided whether the new information indicates a change in behavior or not. If the new information is not significantly different from the old information, then it is decided that there is no change in behavior and the method resumes with step 42. However, if the new information is significantly different from the old information, then it may be decided that there is a change in behavior which indicates a desire to consume food and/or a beverage. As a result, in step 46 the mode is switched, typically from cooling mode to heating mode, but the reverse is also possible. After switching, the method may resume at step 42.

In some embodiments, the switching may not only be between heating and cooling, but may also involve a third or even fourth mode, such as pre-heating and/or pre-cooling. Pre-heating may be carried out in anticipation of heating, while pre-cooling may be used in anticipation of cooling, as indicated by sensor information and/or historical behavioral data. That is, when there are indications that the recipient is about to wake up, for example, but when those indications are not yet strong, a pre-heating mode may be activated. Similarly, when there are indications that the recipient is not about to wake up while the heating mode has already been activated, the pre-cooling mode may be activated. The pre-heating mode may involve active heating, or only the deactivation of cooling.

The recipient of the food and/or beverage, who may also be referred to as consumer, may be a baby, infant or patient. It will be understood that in the present invention a change in the behavior of the recipient, as derived from signals produced by suitable sensors, may cause the switching. In other words, on the basis of data collected by one or more sensors it is decided whether the behavior of the recipient has changed sufficiently to change modes. It will be understood that different threshold values may be used for different types of behavior change, such as volume of sound produced or number of body movements per minute.

The beverages that may be used with the device of the present invention are not limited to milk, and certainly not baby milk, but may also include fruit juices, water, and soup. As baby milk should be kept at about 5° C. and be consumed at about 35° C., baby milk should be heated before consumption. Other beverages or food, such as white wine, may be kept at room temperature but should be slightly chilled before consumption. Food leftovers which were previously heated for consumption should be chilled for later use. The step of switching between the cooling mode and the heating mode may therefore involve switching from the cooling mode to the heating mode or switching from the heating mode (or an inactive mode) to the cooling mode. As mentioned above, the switching may also involve an intermediate mode of pre-cooling or pre-heating.

The present invention utilizes signs indicative of the need for food or drink: sound, movement, vital signs, and/or sleep stage. In addition, the present invention may use stored behavioral data, such as previous feeding session times and optionally also previous feeding session volumes.

Although the present invention has been explained with reference to beverages, it is not so limited and can be also used for foodstuff, such as porridge or other baby food. Applications can be envisaged in which the device is sensitive to a certain spoken word, such as "breakfast!" or "milk!", and will start heating a previously prepared breakfast or beverage in response.

Figure 5:
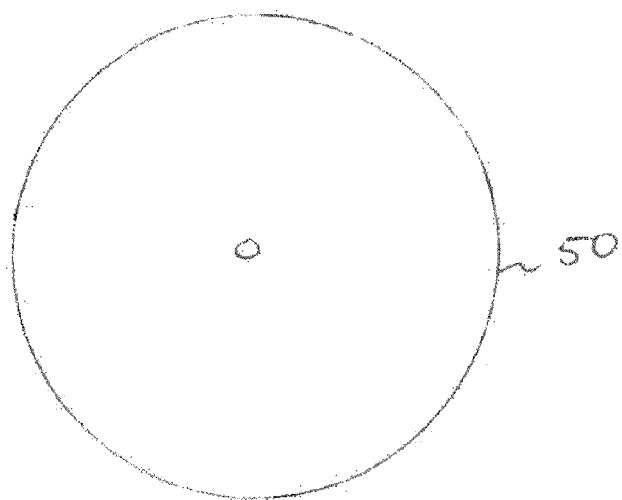
FIG. 5 schematically shows a carrier containing a software program product according to the present invention.

A software program product for causing a processor to carry out the method steps mentioned above is schematically illustrated in FIG. 5. The software program product may be stored on a tangible carrier 50, such as a DVD as illustrated, or a USB stick. Alternatively, the software program product may be stored on a server from which it may be downloaded using the Internet. The software program product contains software instructions which can be carried out by the processor 120 of the device so as to perform the method steps according to the present invention, in particular but not limited to receiving at least one signal indicative of the behavior of the recipient of the food and/or beverage, detecting a change in said behavior based on the at least one received signal, and switching between the cooling mode and the heating mode in response to said detecting.

It will be understood that the description of the invention given above is not intended to limit the invention in any way. Singular nouns and the articles "a" and "an" are of course not meant to exclude the possibility of plurals. Devices mentioned in this document, such as smartphones, may be replaced with their successors, even if these successors are not yet known at the time of writing. As is well established in the law of patents, the abstract should never be used to limit the scope of the claims, and neither should reference numbers in the claims.

It will further be understood by those skilled in the art that the present invention is not limited to the embodiments mentioned above and that many additions and modifications are possible without departing for the scope of the invention as defined in the appending claims.

The invention claimed is:

1. A device for temperature regulation of food and/or beverage, comprising:
   a cooler configured to provide a cooling mode in which the food and/or beverage is cooled;
   a heater configured to provide a heating mode in which the food and/or beverage is heated and for providing a pre-heating mode in which the food and/or the beverage is pre-heated;
   a memory configured to store behavioral pattern data of a recipient of the food and/or beverage;
   a processor configured to predict, using the behavioral pattern data, a future state of a behavior of the recipient of the food and/or beverage; and
   a controller for controlling the cooler and the heater, wherein the controller is configured to:
   receive at least one signal indicative of a current state of the behavior of the recipient of the food and/or beverage,
   detect a change in the current state of the behavior of the recipient of the food and/or beverage,
   activate the cooling mode or the heating mode in response to the detecting of the change in the current state of the behavior of the recipient of the food and/or beverage, and
   activate the pre-heating mode in response to the future state of the behavior predicted by the processor, wherein the pre-heating mode is a mode preceding the heating mode.

2. The device according to claim 1, wherein the at least one signal comprises a sound signal representing sound produced by the recipient.

3. The device according to claim 1, wherein the at least one signal comprises a movement and/or posture signal representing movement and/or posture of the recipient.

4. The device according to claim 1, wherein the at least one signal comprises a vital sign signal representing at least one vital sign of the recipient.

5. The device according to claim 1, wherein the at least one signal comprises a moisture signal representing moisture loss of the recipient.

6. The device according to claim 1, wherein the controller is configured to weigh the at least one signal using the behavior predicted by the processor with a weighting factor.

7. The device according to claim 1, wherein the controller is further arranged to provide an inactive mode in response to the predicted future behavior of the recipient.

8. The device according to claim 1, wherein the controller is configured to selectively respond to sound signals.

9. The device according to claim 8, wherein the controller comprises audio filters and/or a sound recognizer.

10. The device according to claim 1, wherein the controller is configured to detect the change being greater than a threshold, and wherein the threshold is different for different behaviors of the recipient.

11. The device according to claim 1, further comprising at least one sensor configured to produce the at least one signal indicative of the current state of the behavior of the recipient of the food and/or beverage.

12. A method for temperature regulation of food and/or beverage using a cooler for providing a cooling mode in which the food and/or beverage is cooled and a heater for providing a heating mode in which the food and/or beverage is heated and for providing a pre-heating mode in which the food and/or the beverage is pre-heated, the method comprising acts of:
   storing in a memory behavioral pattern data of a recipient of the food and/or beverage;
   predicting, by a processor using the behavioral pattern data, a future state of a behavior of the recipient of the food and/or beverage;
   receiving at least one signal indicative of a current state of the behavior of the recipient of the food and/or beverage;
   detecting a change in the current state of the behavior;
   activating the cooling mode or the heating mode in response to the detecting act; and
   activating the pre-heating mode in response to the future state of the behavior, wherein the pre-heating mode is a mode preceding the heating mode.

13. The method according to claim 12, further comprising an act of providing an inactive mode in response to the future state of the behavior of the recipient.

14. A non-transitory computer readable medium comprising computer instructions which, when executed by a processor, configure the processor to perform a method for temperature regulation of food and/or beverage using a cooler for providing a cooling mode in which the food and/or beverage is cooled and a heater for providing a heating mode in which the food and/or beverage is heated and for providing a pre-heating mode in which the food and/or the beverage is pre-heated, the method comprising acts of:

storing behavioral pattern data of a recipient of the food and/or beverage;

predicting, by the processor using the behavioral pattern data, a future state of a behavior of the recipient of the food and/or beverage;

receiving at least one signal indicative of a current state of the behavior of the recipient of the food and/or beverage;

detecting a change in the current state of the behavior;

activating the cooling mode or the heating mode in response to the detecting act; and activating the pre-heating mode in response to the future state of the behavior, wherein the pre-heating mode is a mode preceding the heating mode.

15. The device of claim 4, wherein the vital sign signal represents a heartbeat or a respiration rate of the recipient.

16. The device of claim 10, further comprising a single temperature regulator, wherein said single temperature comprises a Peltier element.

17. The device of claim 11, wherein the at least one sensor and the controller are connected wirelessly.

18. The method of claim 12, wherein the at least one signal comprises at least one of a sound signal representing sound produced by the recipient, a movement and/or posture signal representing movement and/or posture of the recipient, a vital sign signal representing at least one vital sign of the recipient, and a moisture signal representing moisture loss of the recipient.

19. The method of claim 12, further comprising an act of weighing the at least one signal with a weight factor using the behavior predicted by the predicting act.

20. The method of claim 12, further comprising an act of selectively respond to sound signals included in the at least one signal.

* * * * *